(12) United States Patent
Uchikura et al.

(10) Patent No.: US 7,779,677 B2
(45) Date of Patent: Aug. 24, 2010

(54) LIQUID CHROMATOGRAPHIC ANALYZER AND LIQUID CHROMATOGRAPHY ANALYSIS

(75) Inventors: Kazuo Uchikura, Kanagawa (JP); Kensuke Honda, Yamaguchi (JP); Ikuo Sakurada, Tokyo (JP)

(73) Assignee: Comet Co., Ltd., Kanagawa (JP)

( * ) Notice: Subject to any disclaimer, the term of this patent is extended or adjusted under 35 U.S.C. 154(b) by 274 days.

(21) Appl. No.: 11/817,976

(22) PCT Filed: Mar. 2, 2006

(86) PCT No.: PCT/JP2006/303956

§ 371 (c)(1),
(2), (4) Date: Sep. 7, 2007

(87) PCT Pub. No.: WO2006/095628

PCT Pub. Date: Sep. 14, 2006

(65) Prior Publication Data

US 2008/0271520 A1    Nov. 6, 2008

(30) Foreign Application Priority Data

Mar. 8, 2005    (JP) .................... 2005-063443

(51) Int. Cl.
*G01N 30/00* (2006.01)
(52) U.S. Cl. .................................... 73/61.58
(58) Field of Classification Search ..... 73/61.52–61.58, 73/61.61
See application file for complete search history.

(56) References Cited

U.S. PATENT DOCUMENTS 5,160,419 A    11/1992    Kageyama

FOREIGN PATENT DOCUMENTS

EP    1 055 926 A2    11/2000

(Continued)

OTHER PUBLICATIONS

Akira Fujishima: Kagaku to Kogyo "Chemistry and Industry", vol. 51 (1998), No. 2, pp. 207-209.

(Continued)

*Primary Examiner*—Hezron Williams
*Assistant Examiner*—Tamiko D Bellamy
(74) *Attorney, Agent, or Firm*—Antonelli, Terry, Stout & Kraus, LLP.

(57) ABSTRACT

An apparatus for liquid chromatography which detects ingredients by an electrolytic device, wherein the apparatus can detect many kinds of substances in high sensitivity by making possible to apply a wider range of electrolyzing voltage than former apparatus.

The electrolytic device provided in the apparatus for liquid chromatography has a working electrode which is formed an electrically conductive diamond film on at least one side surface of an electrically conductive plate, a spacer plate of electrical insulating material which is 0.05 to 0.5 mm in thickness and has a hole, and a counter electrode which is facing to the diamond-formed surface of the working electrode while being put the spacer between the electrodes. Furthermore, an eluate inlet hole, an eluate outlet hole and a reference electrode are opened to a cavity formed by the hole of the spacer plate, and the eluate in the electrolytic device is pressurized to 1.0 to 15.0 kg/cm$^2$.

12 Claims, 3 Drawing Sheets

FOREIGN PATENT DOCUMENTS

| | | |
|---|---|---|
| JP | 62-197758 | 9/1987 |
| JP | 04-089561 | 3/1992 |
| JP | 05-296964 | 11/1993 |
| JP | 10-019839 | 1/1998 |
| JP | 2001-050924 | 2/2001 |
| JP | 2003-262612 | 9/2003 |
| JP | 2004-195391 | 7/2004 |
| JP | 2005-021744 | 1/2005 |
| JP | 2005195489 A * | 7/2005 |

OTHER PUBLICATIONS

Kensuke Honda, et al.: Shokubai, "Catalyst", vol. 41 (1999), No. 4, pp. 264-269.

Heldi B. Martin, et al.: J. Electrochem. Soc. vol. 143 (1996), No. 6, pp. L133-L136.

L. Boonma, et al.: J. Electrochem. Soc. vol. 144 (1997), No. 6, pp. L142-L145.

International Report on Patentability for Application No. PCT/JP2006/303956, dated Sep. 20, 2007.

Translation of the International Preliminary Report on Patentability for Application No. PCT/JP2006/303956, dated Sep. 20, 2007.

* cited by examiner

LIQUID CHROMATOGRAPHIC ANALYZER AND LIQUID CHROMATOGRAPHY ANALYSIS

TECHNICAL FIELD

The present invention relates to an apparatus for liquid chromatography which uses an electrolytic device as means for detecting ingredients in eluate. Furthermore, it relates to a method for analysis of several organic compounds by making use of the apparatus.

BACKGROUND ART

There is liquid chromatography as one of the methods to analyze ingredients in liquid which contains several organic compounds. As the liquid chromatography, high-speed liquid chromatography (HPLC), which uses packing materials of improved particle-size distribution for the separation column, is widely adopted now. The above method uses several detecting means for detecting ingredients in eluate which flows out from the separation column. As a general one, for instance, there is a differential refractometer. Though this can be used all-roundly, it has problems that it lacks selectivity in kinds of substances and it has not so high sensitivity. On the other hand, an ultraviolet absorption detector is most popular among selective detectors; however, it cannot be applied to compounds such as alcohols, which do not show effective ultraviolet absorption. For this reason, the method, which analyzes derivatives being combined with ultraviolet-absorbing groups, is conducted, however, this method is complicated. Also there are a fluorescence detector and a chemical luminescence detector among selective detectors. Though they can detect specific compounds in high sensitivity, the scope of compounds to be detected is more limited.

Furthermore, there is an electrochemical detector as shown in the patent document JP-A-5-296964 (Hei) for the detector to be used in HPLC. This is applied for the analysis of catecholamines and so on, as explained in the above patent document concerning the analysis of physiologically active substances and metabolites of creatures. The above patent document is explaining that its coulometric detector, the active electrode of which uses glassy carbon having small pores of 1 to 100 μm in diameter on its surface, has far higher sensitivity in the electrochemical conversion characteristic than the former detectors using porous graphite.

Patent Document 1: JP-A-5-296964(Hei)

DISCLOSURE OF THE INVENTION

Problem to be Solved by the Invention

Concerning the apparatus shown in the above JP-A-5-296964 (Hei) which uses the electrochemical detector for the HPLC, the document mentions analysis of catecholamines, serotonin and their metabolites as the application examples; however, it does not mention analysis of another organic compounds. The reason is that the above apparatus cannot be applied to wide kinds of substances, for instance, organic acids. Namely, the oxidizing reaction of the substances to be detected by the electrochemical detector should be conducted below the voltage at which electrolysis of water occurs, in other words, within the range of a potential window. However, the oxidizing reaction does not occur for many organic compounds below the voltage at which electrolysis of water occurs by the above apparatus. For solving the above problem, this invention aims to provide a method for detecting many kinds of substances with high sensitivity by making possible to apply wider range of the electrolyzing voltage than the range hitherto, in the analysis by the electrochemical detector for the HPLC.

Means for Solving the Problem

The apparatus for liquid chromatography in accordance with the present invention for solving the above problem, which is equipped with an electrolytic device in a passage of eluate from a separation column, is characterized in that the electrolytic device has a working electrode which is formed an electrically conductive diamond film on at least one side surface of an electrically conductive plate, a spacer plate of electrical insulating material which is 0.05 to 0.5 mm in thickness and has a hole, and a counter electrode which is facing to the diamond-formed surface of the working electrode while the spacer plate is placed between the working electrode and the counter electrode; that the electrolytic device has an eluate inlet hole, an eluate outlet hole and a reference electrode, which are opened to a cavity formed by the hole of the spacer plate; that the eluate in the electrolytic device is pressurized to 1.0 to 15.0 $kg/cm^2$; and that a measuring device, which measures electrolysis current while electrolyzing by applying a constant voltage to the working electrode, is connected to the electrolytic device.

Also the above apparatus is characterized in that the diamond film is not formed on plate-end surfaces of the working electrode, and that the electrolytic device has structure that the eluate is allowed to contact to all surfaces of the working electrode except a part of an opposite surface to the surface facing to the counter electrode. And also, the apparatus is characterized in that two or more of the electrolytic devices are connected in series in the passage of eluate, and that the measuring device measures electrolysis current respectively while electrolyzing by applying to the working electrodes respectively constant voltages, which are higher in order at the electrolytic devices of downstream sides.

The method for liquid chromatography in accordance with the present invention, wherein ingredients are detected by introducing eluate from a separation column into an electrolytic device, is characterized in that a working electrode of the electrolytic device is an electrically conductive plate on which an electrically conductive diamond film is formed, and that detection of ingredients is conducted by measurement of electrolysis current by electrolyzing at a voltage higher than 1.4V to a standard hydrogen cell.

ADVANTAGEOUS EFFECT OF THE INVENTION

In the apparatus for liquid chromatography in this invention, the electrolytic device, which detects ingredients in eluate from the separation column, is able to conduct electrolysis by applying a higher voltage than the voltage hitherto, by adopting a diamond electrode for the working electrode. Therefore, the scope of compounds to be analyzed can be expanded to the compounds which are not electrolyzed by a low voltage which can be applied in the former apparatus using carbon electrodes. Hereupon, analysis for trace amounts of ingredients has been made possible by the construction, wherein the working electrode and the counter electrode are faced with a small gap. Moreover, this invention makes possible to lower costs, because the apparatus can adopt the working electrode, wherein not all surfaces of a thin plate for substrate are coated with diamond, but the plate is naked at such as the edge surfaces.

EXPLANATION OF REFERENCES

Figure 1:
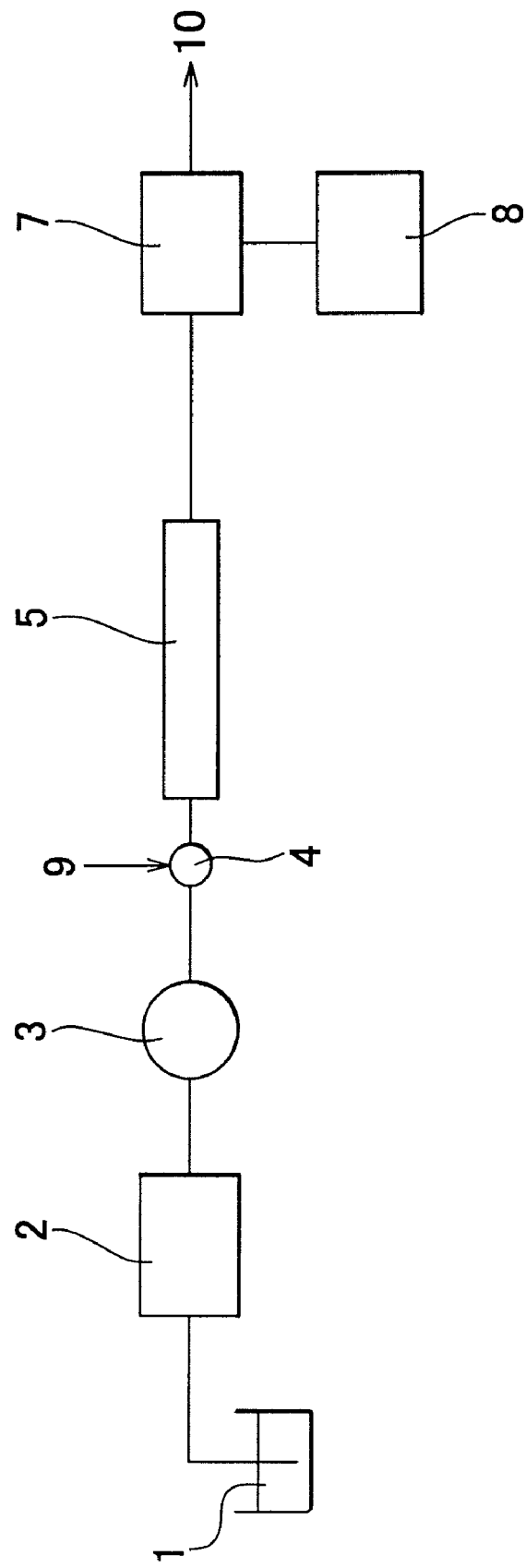
FIG. 1 Schematic view showing construction of the apparatus for liquid chromatography of this invention FIG. 2 Cross-sectional view parallel to the axis showing the electrolytic device for the liquid chromatography of this invention FIG. 3 A-A' arrow cross-sectional view of FIG. 2

1 Eluate
2 Degasser
3 Pump
4 Injector
5 Separation column
7 Electrolytic device
8 Measuring device
9 Sample for analysis
10 Flowing-out liquid
11 Working electrode
12 Spacer
121 Hole
13 Counter electrode
14 Space
15,16 Eluate inlet hole and eluate outlet hole
17,18 Fittings
19 Conducting terminal
20 Conducting plate
21 Conducting terminal
22 Pressurizing cover
23,24,25,26 O-rings
27 Insulating cover
30 Reference electrode
301 Container
302 Electrolyte
303 Electrode material
304 Filter
305 Lid
306 O-ring

BEST MODE FOR CARRYING OUT THE INVENTION

FIG. 1 is a schematic view showing construction of the apparatus for liquid chromatography of this invention. Eluate 1 is fed into a separation column 5 in a constant speed by a pump 3 through a degasser 2 which eliminates dissolved gas by pressure reduction. Numeral 4 is an injector which injects a determined amount of sample for analysis 9 into the separation column. The eluate from the separation column 5 is fed into an electrolytic device 7, and then, discharged as flowing-out liquid 10. A constant voltage is applied between the electrodes of the electrolytic device, and then, electrolysis current by ingredients in the solution occurs at every time when electrochemically active substance flows out from the separation column. The signal of the electrolysis current is transmitted to a measuring device 8. Other than the electrolysis current itself, the measuring device can output coulometric data which is a time sum of the electrolysis current, so that it makes possible quantitative analysis. The measurement of electrolysis current mentioned in this invention includes such coulometric measurement.

For the separation column 5, it is favorable that the difference in absorptive power among each of the analyzing ingredients is large. As a general one, reversed phase chromatography using ODS silica can be adopted. Also columns of polymer-system ion-exchange type, normal-phase amino-group combined type and so on can be adopted corresponding to the substances to be analyzed. For the eluate, such solution, wherein buffer solution as phosphate buffer and so on is mixed to acetonitrile or methanol, can be adopted. Also buffer solution of several kinds can be used for the ion-exchange type column.

Figure 2:
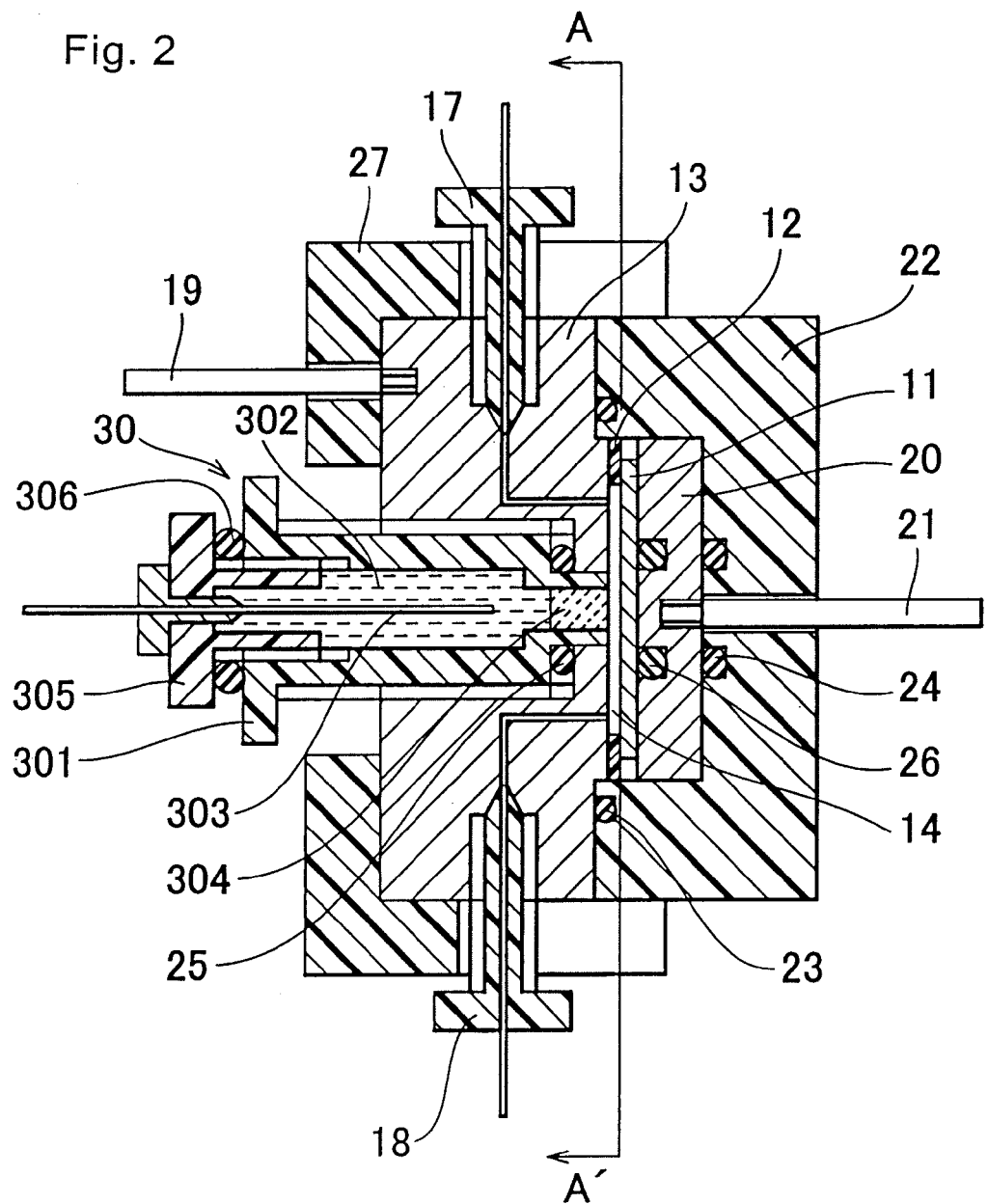
Figure 3:
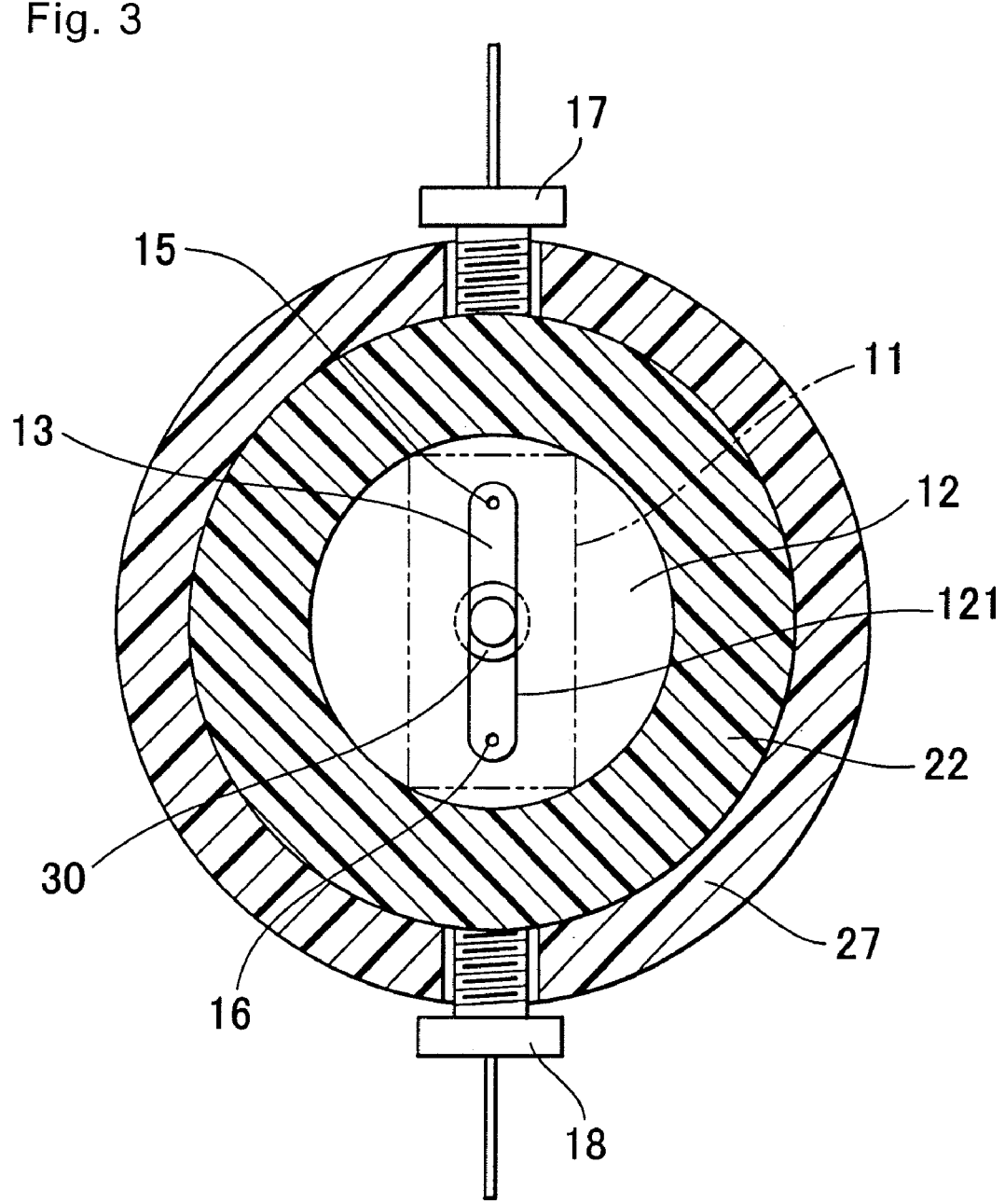

FIG. 2 and FIG. 3 are showing the electrolytic device for the liquid chromatography of this invention, wherein FIG. 2 is a cross-sectional view parallel to the axis and FIG. 3 is an A-A' arrow cross-sectional view of FIG. 2. In these drawings, 11 is a working electrode (in FIG. 3 positional relationship is shown by double-dotted chain line), wherein an electrically conductive diamond film is formed at least on the front surface, namely, on the left side surface in FIG. 2 of the substrate made of an electrically conductive thin plate. Numeral 12 is a spacer, which is made of chemical-resistant insulating material such as fluororesin, and has a long-shaped hole 121 as shown in FIG. 3. Numeral 13 is a counter electrode, which is made of an electrically conductive anticorrosive block such as titanium, and is facing the diamond coated surface of the working electrode, whereby the spacer 12 is put between the electrodes. Besides, the part, which acts as the counter electrode in the electrically conductive block, is the area which is facing the working electrode. Therefore, so long as at least the above part is electrically conductive, the whole block should not always be electrically conductive, but the block may be made by combination of electrically conductive material and insulating material which are constructed to the shape of the block.

As opened into a space 14 which is formed by the hole 121 of the above-mentioned spacer 12, there are an inlet hole 15 and an outlet hole 16 of eluate, and a reference electrode 30, each of which is provided in the block of the counter electrode 13. Namely, the inlet hole 15 and the outlet hole 16 of eluate are formed by drilling holes into the block of the counter electrode 13, and then, fittings 17 and 18 for introducing and discharging the eluate are screwed into the block of the counter electrode. Also the reference electrode 30 is fit by screwed into the block of the counter electrode, so that the head surface of the reference electrode and the acting surface of the counter electrode are in a same plane. Besides, numeral 19 is a conducting terminal to the counter electrode 13.

At the back side of the working electrode 11, namely, the opposite surface of the surface which is facing to the counter electrode 13, a conducting plate 20 is provided which is touching the working electrode 11. The conducting plate is made of anticorrosive metal, because it contacts the eluate as explained later. Numeral 21 is a conducting terminal to the working electrode 11, wherein the terminal is combined with the conducting plate 20. Numeral 22 is a pressurizing cover which is made of electrically-insulating chemical-resistant material and is combined with the above-mentioned block of the counter electrode 13 by plural setscrews not shown in the drawings. The pressurizing cover 22 has functions for retaining the electrode part of the electrolytic device and also holding the interior of the electrolytic device in a pressurized state. Therefore, O-rings 23 and 24 are inlayed so that the electrode part in which the eluate flows is sealed. In order to keep the interior of the electrolytic device in pressurized state as above-mentioned, also an O-ring 25 for sealing is provided for the fitting part of the reference electrode 30, furthermore, O-rings 26 and 306 are provided for the conducting plate 20 and the reference electrode 30 itself, which will be explained later. Numeral 27 is an insulating cover made of plastics, which is inserted from the left side of FIG. 2 and combined with the metal block of the counter electrode by plural setscrews not shown in the drawings.

As the reference electrode 30, an example of Ag—AgCl system is shown, wherein the electrolyte 302, which is made of saturated KCl solution gelated by gelatin, is filled in a chemical resistant such as fluororesin container 301. Furthermore, into the container, Ag wire which is coated with AgCl is inserted as an electrode material 303. Numeral 304 is a filter such as porous ceramics, which separates between the electrolyte 302 of the reference electrode and the eluate which is the solution to be measured. An O-ring 306 is fitted between the container 301 and the lid 305 of the reference electrode in order to seal the electrolyte 302, because the interior of the reference electrode is pressurized as being caused by the pressurization of interior of the electrolytic device. Besides, the reference electrode in this invention is not limited to the Ag—AgCl system, but another systems can be adopted. The above-mentioned reference electrode is 0.199V at 25° C. to the standard hydrogen electrode (NHE). For the reference electrode of another kinds the voltage can be converted according to its electromotive force.

As above explained, the electrolytic device of this invention uses the electrically conductive diamond electrode for the working electrode 11. It is made by forming a diamond film on the substrate of an electrically conductive thin plate. For the electrically conductive thin plate, an electrically conductive single-crystal silicon plate, the surface of which is polished, is adopted ordinarily, and also such as titanium can be used. It's dimension is 0.7 mm or so in thickness and the face dimension can be, for instance, an oblong which is a size larger than the hole 121 of the spacer 12 as shown in FIG. 3, nevertheless, it is not limited so long as the face is larger than the hole of the spacer and the plate can be accommodated in the prescribed position of the device. This plate is placed in a reaction chamber for plasma assisted CVD, then microwave discharge is occurred in hydrogen atmosphere containing carbon source at a vacuum of about 100 Torr. The carbon source is, for instance, a mixture of acetone and methanol in which a trace content (for instance, boron/carbon ratio of 1%) of boron oxide is dissolved for doping boron. The substrate plate is heated to about 900° C. by the microwave discharge and a film is formed gradually which is composed of fine diamond crystals of a few micrometers. The diamond film is formed until about 30 μm in thickness ordinarily. By the above method, the diamond film is formed on the front surface and the edge surfaces of the thin plate, and to some extent, on the back surface under some conditions. To be explained later, also there is another method, wherein the diamond film is formed on a plate of a large dimension, and then, the plate is divided into the dimension of the working electrode.

The electrolytic device, which detects ingredients of the eluate, for liquid chromatography in this invention can conduct the electrolysis at higher voltage than former devices, by using the diamond electrode for the working electrode as described above. Namely, by the electrode of carbon material such as glassy carbon, which is used ordinarily for the working electrode in electrolytic devices hitherto, it is difficult to measure the electrolysis current by the ingredients, because electrolysis of water occurs at the anode potential over 1.4V to the standard hydrogen electrode (called "NHE" hereafter). On the other hand, by using the diamond electrode as the working electrode, electrolysis of water does not occur at higher voltage. According to measurement by the inventors concerning the diamond electrode, which had been made by the above-explained method, electrolysis of water did not occur until 2.7V (to NHE). Therefore, the apparatus for liquid chromatography in this invention makes possible to detect substances which could not be detected formerly because of high electrolytic potential.

As mentioned before, the diamond-formed surface of the working electrode 11 is facing to the counter electrode 13, while the spacer plate is placed between the working electrode and the counter electrode. The speed of the electrolytic reaction can be made high enough, whereby the wide area of the diamond electrode surface for the working electrode contributes to the electrolysis effectively. Moreover, the electrode surface of the counter electrode 13 is facing to the working electrode by the narrow gap which is separated by the spacer 12. In a common electrolytic device which uses the carbon electrode or the like, usually the counter electrode is placed at a distance from the working electrode nevertheless the working electrode itself has a wide surface area, in order to utilize a metal fitting in the eluate passage simultaneously for the counter electrode.

An adequate thickness of the above spacer 12 is from 0.05 to 0.5 mm. In order to make possible to analyze trace ingredients, it is important that a whole area of the working electrode 11 is facing an electrode surface of the counter electrode 13 by such a narrow gap. By this arrangement a detectable electrolysis current can be obtained, even if ingredients to be detected by electrolysis are trace amount. One of the reasons is assumed that the ratio of eluate which flows out while not contributing electrolysis decreases by the passage in front of the working electrode surface being narrower, because the electrolysis occurs in the liquid near to the working electrode surface. However, the reason of some effects such as the effect of the counter electrode being near to the working electrode cannot be explained thoroughly by the present theories. If the thickness of the above-mentioned spacer is less than 0.05 mm, the working electrode and the counter electrode might touch and resistance of the eluate flow becomes too high. On the other hand, if the thickness is over 0.5 mm, the sensitivity in detecting trace ingredients becomes lower.

As explained before, the interior of the electrolytic device of this invention is sealed by the O-rings 23 and 24 which are inlayed in the pressurizing cover 22. Thus, the eluate flows into the area which is shut by the O-rings, therefore, even the back surface, which is not formed diamond, of the working electrode 11 contacts with the eluate. Accordingly, in order to keep direct electrical contact between the back surface and the conducting plate 20 while not intervened by the eluate, an O-ring 26 is set to the conducting plate around a part to be electrically conducted to the electrode plate so that the eluate does not flow into inside of the O-ring. As explained before, also the O-ring 25 is provided for sealing to the fitting part of the reference electrode 30, and the O-ring 306 is provided to the reference electrode itself so that the electrolyte does not leak at pressurized state inside.

The eluate in the electrolytic device is pressurized to 1.0 to 15.0 kg/cm$^2$ (gage pressure). The reason why the interior of the electrolytic device is pressurized is to minimize the influence of electrolysis of water which occurs at the back surface and end surfaces, which are not formed diamond, of the plate of the working electrode 11, and at the surfaces of the conducting plate 20. Namely, at the no-diamond-coated surfaces of the plate of the working electrode 11 and the surfaces of the conducting plate 20, which is made of titanium or the like, the electrolysis of water naturally occurs at a high voltage which can be applied to the electrolytic device in this invention. However, the current mostly stop after the electrolysis has progressed to some extent after switching on the electrolytic device, and then, this state is maintained during the analysis using the electrolytic device. The reason of this is presumed that the surface of the metal is covered by a film of gas which is generated by the electrolysis, because the liquid is staying at the above-mentioned places. Nevertheless, it is difficult to maintain always stably the state that the electrolysis of water is stopped, therefore, occasionally the phenomenon of disturbance to the measured value, which was caused by the electrolysis of water, was observed. Then, experiments of the inventors revealed that the electrolysis of water can be stopped stably by pressurizing the interior of the electrolytic device. Besides, the theoretical basis of this effect is unknown at present.

If the pressure of the pressurizing is less than 1.0 kg/cm$^2$, the above-explained effect becomes insufficient. On the other hand, if the pressure is more than 15.0 kg/cm$^2$, sealing of the device becomes difficult. The pressurizing of the interior of the electrolytic device can be attained by providing a flow resistance means such as a capillary of an adequate length to the eluate exit from the electrolytic device. Besides, plural electrolytic devices are sometimes joined in series in the liquid passage. In this case the flow resistance means may be provided only to the exit of the last electrolytic device. By this method, pressures in the electrolytic devices of the former stages become higher to some extent by flow resistance; nevertheless it should be taken care that pressures of all of the electrolytic devices are within the above-described range.

By maintaining the pressurized state for the interior of the electrolytic device, it has been made possible to use the diamond-coated electrode plate which is divided from a large plate, and then, to lower cost of the apparatus. Namely, the diamond-coated electrode plate is expensive, but the cost does not vary so much for the area of the plate, therefore, making use of a large plate for dividing can lower the cost. However, the substrate material is bared at the edge surfaces of the electrode plate which is divided from a large plate after formed a diamond film, contrary to that the diamond film is formed on the edge surfaces of the electrode plate as same as the front surface, wherein the diamond film is formed on the substrate prepared for the electrode size. When the plate in which the substrate material is bared at the edge surfaces as above is used, the stopped state of the electrolysis of water is apt to unstable; nevertheless, the electrolysis of water can be stopped stably by pressurizing the interior of the electrolytic device.

Besides, it might be thought simply that the above-explained problem concerning the electrolysis of water can be solved thoroughly; so long as the eluate does not leak out of the space which is formed by the working electrode 11, the counter electrode 13 and the hole 121 of the spacer, so that the electrolysis is limited within the diamond-formed surface. Namely, prevention of leak of the eluate along the surfaces of the spacer will solve the problem. Then, in order to enhance the sealing effect on the surfaces of the spacer, high pressure should be exerted between the working electrode 11 and the counter electrode 13. However, this attempt was not successful because the pressure within the limit, in which the plate of the working electrode 11 was not damaged, could not prevent the leak. Therefore, the electrolytic device of this invention employs countermeasure against the electrolysis of water, while adopting the structure which allows that the whole plate surfaces of the working electrode 11 contacts the eluate, except a part of the opposite surface of the surface facing to the counter electrode 13, namely, the electrically contacting area to the conducting plate 20.

The above-described electrolytic device is supplied continuously with the eluate from the isolation column while being set in a certain condition, and then, detects ingredients in the liquid successively. The most common condition for electrolysis is to apply a constant voltage between the working electrode and the counter electrode, and then, to detect ingredients in the eluate from the isolation column successively by measuring and recording the change of the electrolysis current. As mentioned before, by using the diamond electrode for the working electrode, the electrolytic device in this invention can electrolyze at higher voltage than former devices. Therefore, it makes possible to analyze compounds which could not be detected by electrolysis hitherto.

On the other hand, the high electrolyzing voltage sometimes makes difficult to identify compounds by increasing kinds of the detected compounds, because the oxidizing reaction itself by electrolysis has not specific selectivity among the kinds of compounds. This problem can be solved by connecting two or more of the electrolytic devices in series in the passage of eluate, electrolyzing by applying to the working electrodes respectively higher voltages in order at the electrolytic devices of downstream sides, and then, measuring electrolysis current of the each electrolytic device by the measuring device. For instance, in case of connecting two electrolytic devices, they can detect compounds while discriminating between the compounds which can be electrolyzed below a certain voltage and the compounds which can be electrolyzed only at a higher voltage than that. Further, by connecting three or more of the electrolytic devices, they can detect in a state of being more classified by voltage ranges to be electrolyzed. Besides, in electrolytic devices of the upstream side, sometimes a voltage is adopted wherein the electrolysis of water does not occur by using even a carbon electrode. However, for all of the electrolytic devices it is favorable to use the devices of this invention which use the diamond electrodes, because inner pressure cannot be raised so much in the ordinary electrolytic devices. Namely, at the electrolytic devices connected in series, if the interior of the downstream-side device is pressurized, the devices of the upstream side than that become pressurized states.

As above-explained, by the apparatus for liquid chromatography in this invention, electrolysis at a voltage higher than 1.4V to the standard hydrogen cell can be conducted, which cannot be conducted by ordinary working electrodes using carbon material owing to the electrolysis of water. By applying a voltage higher than 1.4V to the standard hydrogen cell as above, a hydroxyl group, a carboxyl group, a peroxyd group, an amino group, a mercapto group and so on in organic compounds in solution can be detected. Accordingly, organic compounds which have one or more of one kind among the above-mentioned groups can be detected, and also, organic compounds which have two or more kinds simultaneously among these groups can be detected. Many of these organic compounds could not be detected by former electrolytic devices, because the electrolytic potentials of these compounds are higher than the electrolytic potential of water. Moreover, some of these compounds could hardly be analyzed hitherto, because there was not another adequate method to detect them.

Among the above organic compounds, as the compounds which have the hydroxyl group, there are, for instance, a sort of alcohols such as methanol, ethanol, ethylene glycol, glycerin and so on, and a sort of phenols. As the organic compounds which have the carboxyl group, there are monocarbonic acids such as propionic acid, acetic acid, butyric acid, valeric acid, benzoic acid and so on, dicarbonic acids such as succinic acid, adipic acid and so on, tricarbonic acid such as citric acid and so on, and hydroxycarbonic acid such as malic acid, succinic acid and so on. And also sodium salt and potassium salt of the above acids are included as the compounds which have the carboxyl group. As the organic compounds which have the amino group, there are, for instance, methylamine, ethylamine and so on, and amino acids such as alanine, glycine and so on. As the organic compounds which have the peroxy group, for instance, ethane peroxy acid, propane peroxy acid, perbenzoic acid and soon can be cited. As the organic compounds which have the mercapto group, for instance, mercaptoacetic acid, mercaptoethanol and so on can be cited.

Also the apparatus for liquid chromatography in this invention can detect an ether bond, an ester bond, a disulfide bond and so on in organic compounds in solution. Organic compounds which have one or more of one kind among the above bonds and so on can be detected, and also, organic compounds which have two or more kinds simultaneously among these bonds can be detected. Many of these organic compounds could not be detected by former electrolytic devices, because the electrolytic potentials of these compounds are higher than the electrolytic potential of water. As the organic compounds which have the ether bond, there are, for instance, diethylether, ethylene glycol monomethylether, guaiacol, anisole and soon. As the organic compounds which have the ester bond, there are, for instance, ethyl acetate, methyl isobutyrate, dimethyl malonate, triethyl citrate and so on. As the organic compounds which have the disulfide bond, there are, for instance, diphenylsulfane, diacetylsulfane and so on.

The apparatus for liquid chromatography in this invention is especially suitable for analyzing nonionic surface active agent. As typical nonionic surface active agents, there are compounds which have an ether bond or an ester bond such as alkyl polyoxyethylene ether $(RO(CH_2CH_2O)_nH)$, fatty acid polyoxyethylene ester $(ROO(CH_2CH_2O)_nH)$ and so on, and compounds which have hydroxyl group such as fatty acid monoethanolamide $(RCONHCH_2CH_2OH)$, fatty acid diethanolamide $(RCON(CH_2CH_2OH)_2)$ and so on. The apparatus of this invention can analyze the above nonionic surface active agent in especially higher sensitivity than former analyzing methods, though these compounds belong to the aforementioned organic compounds to be analyzed by the apparatus of this invention.

EXAMPLES

Analysis was conducted by the apparatus shown in FIG. 1. For the eluate 1, 100 mMol-$KH_2PO_4$+10% acetonitrile of water solution was fed at a speed of 0.5 ml/min. For the column 4, an ion-exchange type column of 4.6 mm inner diameter and 250 mm length was used. The electrolytic device 7, which used boron-doped diamond for the working electrode, had the construction shown FIG. 2 and FIG. 3. The electrolytic device was connected to the coulometer-type measuring device 8, which recorded the electric current with the time lapse by applying a constant voltage to the working electrode.

The applying voltage to the working electrode of the electrolytic device was set at 2.5V (to the Ag/AgCl standard cell, same hereafter), nevertheless, electrolysis of water did not occur. A sample which contained methanol, ethanol and 2-propanol at a concentration of 1 pmol/µl respectively was injected from the injector 4 at an amount of 20 µl, then, peaks of electrolysis current of the each component were detected. When the applying voltage to the working electrode was decreased to 1.15V, which can be applied to the ordinary glassy-carbon electrode without occurrence of the electrolysis of water, electrolysis current was not detected, though the above sample solution was injected to the injector. Also under a similar condition, a sample, which contained ethylamine, alanine and glycine at a concentration of 1 pmol/µl respectively, was injected from the injector 4 at an amount of 20 µl. Then, peaks of electrolysis current of the each component were detected at 2.5V for the applying voltage to the working electrode, however, not detected at 1.15V.

Among the above-described conditions, the column 4 was changed to a column of 4.6 mm inner diameter and 150 mm length being packed with ODS-silica. Then, 100 mMol-$KH_2PO_4$+10% acetonitrile of water solution was used as the eluate 1, the applying voltage to the working electrode was set at 2.5V, and the other conditions were same as the above example. A sample which contained acetic acid, succinic acid, citric acid and potassium laurate at a concentration of 1 pmol/µl respectively was injected from the injector 4 at an amount of 20 µl, then, peaks of electrolysis current of the each component were detected. When the applying voltage to the working electrode was decreased to 1.15V, electrolysis current was not detected, though the above sample solution was injected to the injector. Also under a similar condition, a sample, which contained diethyl ether, ethylene glycol monomethyl ether and ethyl acetate at a concentration of 1 pmol/µl respectively, was injected from the injector 4 at an amount of 20 µl. Then, peaks of electrolysis current of the each component were detected at 2.5V for the applying voltage to the working electrode, however, not detected at 1.15V.

INDUSTRIAL APPLICABILITY

By the apparatus for liquid chromatography of this invention, electrolysis of water does not occur in detecting ingredients by electrolysis, by applying a higher voltage than the voltage applicable to the former apparatus which uses carbon material for the working electrode. Accordingly, compounds, which have been beyond the scope of analysis by electrolysis because their electrolytic potential is higher than that of water, can be detected. Therefore, the apparatus makes wider the scope of objects for analysis.

The invention claimed is:

1. An apparatus for liquid chromatography, wherein the apparatus is equipped with an electrolytic device in a passage of eluate from a separation column, characterized in that the electrolytic device comprises a working electrode which is formed an electrically conductive diamond film on at least one side surface of a electrically conductive plate, a spacer plate of electrical insulating material which is 0.05 to 0.5 mm in thickness and has a hole, and a counter electrode which is facing to the diamond-formed surface of the working electrode while the spacer plate is placed between the working electrode and the counter electrode; that the electrolytic device has an eluate inlet hole, an eluate outlet hole and a reference electrode, which are opened to a cavity formed by the hole of the spacer plate; that the eluate in the electrolytic device is pressurized to 1.0 to 15.0 kg/cm$^2$; and that a measuring device, which measures electrolysis current while electrolyzing by applying a constant voltage to the working electrode, is connected to the electrolytic device.

2. The apparatus for liquid chromatography according to claim 1, characterized in that the diamond film is not formed on plate-end surfaces of the working electrode.

3. The apparatus for liquid chromatography according to claim 1 or 2, characterized in that the electrolytic device has structure that the eluate is allowed to contact to all surfaces of the working electrode except a part of an opposite surface to the surface facing to the counter electrode.

4. The apparatus for liquid chromatography according to claim 1, characterized in that two or more of the electrolytic devices are connected in series in the passage of eluate, and that the measuring device measures electrolysis current respectively while electrolyzing by applying to the working electrodes respectively constant voltages, which are higher in order at the electrolytic devices of downstream sides.

5. A method for analysis by liquid chromatography, wherein ingredients are detected by introducing eluate from a separation column into an electrolytic device, characterized in that a working electrode of the electrolytic device is an electrically conductive plate on which an electrically conductive diamond film is formed, and that detection of ingredients is conducted by measurement of electrolysis current by electrolyzing at a voltage higher than 1.4V to a standard hydrogen cell.

6. The method for analysis by liquid chromatography according to claim 5, wherein the method analyze at least one of a hydroxyl group, a carbonyl group, an amino group, a peroxy group and a melcapt group in organic compounds.

7. The method for analysis by liquid chromatography according to claim 5, wherein the method analyze at least one of an ether bond, an ester bond and a disulfid bond.

8. The method for analysis by liquid chromatography according to claim 5, wherein the method analyze a nonionic surface-active agent.

9. An apparatus for liquid chromatography, comprising:
a separation column arranged to receive a sample of eluate;
an electrolytic device arranged to conduct an electrolysis and to detect ingredients in the eluate from the separation column for liquid chromatography; and
a measuring device connected to the electrolytic device, to measure an electrolysis current and a change of the electrolysis current for quantitative analysis of the ingredients in the eluate,
wherein the electrolytic device comprises a working electrode formed by an electrically conductive diamond film on at least one side surface of an electrically conductive plate; a spacer plate of an electrical insulating material exhibiting a thickness of 0.05 to 0.5 mm; and a counter electrode arranged to face the diamond-formed surface of the working electrode while the spacer plate is placed between the working electrode and the counter electrode;
wherein the electrolytic device is pressurized to 1.0 to 15.0 $kg/cm^2$; and
wherein the measuring device measure the electrolysis current while electrolyzing by applying a constant voltage between the working electrode and the counter electrode.

10. The apparatus for liquid chromatography according to claim 9, wherein the diamond film is not formed on plate-end surfaces of the working electrode.

11. The apparatus for liquid chromatography according to claim 9, wherein the electrolytic device has a structure that the eluate is allowed to contact to all surfaces of the working electrode, except a part of an opposite surface to the surface facing to the counter electrode.

12. The apparatus for liquid chromatography according to claim 9, further comprising two or more of the electrolytic devices connected in series in a passage of eluate, wherein the measuring device measures the electrolysis current respectively while electrolyzing by applying to the working electrodes and counter electrodes respectively constant voltages, which are higher in order at the electrolytic devices of a downstream side.

\* \* \* \* \*